US010012577B2

(12) United States Patent
Zhou et al.

(10) Patent No.: US 10,012,577 B2
(45) Date of Patent: Jul. 3, 2018

(54) ROCK HOLLOW CYLINDER TORSIONAL SHEAR APPARATUS

(71) Applicant: Institute of Rock and Soil Mechanics, Chinese Academy of Sciences, Wuhan, Hubei (CN)

(72) Inventors: Hui Zhou, Hubei (CN); Jingjing Lu, Hubei (CN); Dawei Hu, Hubei (CN); Chuanqing Zhang, Hubei (CN); Yue Jiang, Hubei (CN); Lei Huang, Hubei (CN); Fanjie Yang, Hubei (CN); Yong Zhu, Hubei (CN); Yang Gao, Hubei (CN)

(73) Assignee: Institute of Rock and Soil Mechanics, Chinese Academy of Sciences, Wuhan (CN)

( * ) Notice: Subject to any disclaimer, the term of this patent is extended or adjusted under 35 U.S.C. 154(b) by 0 days.

(21) Appl. No.: 15/622,056

(22) Filed: Jun. 13, 2017

(65) Prior Publication Data
US 2018/0136099 A1  May 17, 2018

(30) Foreign Application Priority Data

Nov. 14, 2016  (CN) .......................... 2016 1 1008936

(51) Int. Cl.
*G01N 3/02* (2006.01)
*G01N 3/24* (2006.01)
*G01N 3/22* (2006.01)

(52) U.S. Cl.
CPC ................ *G01N 3/22* (2013.01); *G01N 3/02* (2013.01); *G01N 3/24* (2013.01); *G01N 2203/0021* (2013.01); *G01N 2203/0075* (2013.01)

(58) Field of Classification Search
CPC ............ G01N 3/08; G01N 2203/0016; G01N 2203/028; G01N 2203/0617; G01N 2203/067; G01N 3/38; G01N 2203/0017; G01N 2203/0423; G01N 2203/0635; G01N 2203/0682
See application file for complete search history.

(56) References Cited

U.S. PATENT DOCUMENTS

| 5,005,424 A * | 4/1991 | Markowski | G01N 3/04 73/834 |
| 5,025,668 A * | 6/1991 | Sarda | G01N 3/10 73/795 |
| 5,302,023 A * | 4/1994 | Larsen | G01N 3/18 374/46 |
| 2005/0022608 A1* | 2/2005 | Moscrip | G01N 3/08 73/818 |
| 2009/0314107 A1* | 12/2009 | Yakimoski | G01N 3/08 73/865.6 |
| 2014/0123773 A1* | 5/2014 | Lemmer | G01K 13/12 73/863.01 |

* cited by examiner

Primary Examiner — Harshad R Patel
Assistant Examiner — Brandi Hopkins

(57) ABSTRACT

The present invention belongs to the technical field of rock mechanics testing equipment, and discloses a rock hollow cylinder torsional shear apparatus which includes a frame, a lifting device, a bottom seat, a confining pressure barrel, an upper seat, a force transmission shaft, a force transmission shaft holder, a torque application structure and a controller. The present invention provides a torsional shear apparatus capable of avoiding mutual interference between axial force application and torque force application.

18 Claims, 2 Drawing Sheets

US 10,012,577 B2

ROCK HOLLOW CYLINDER TORSIONAL SHEAR APPARATUS

CROSS-REFERENCE TO RELATED APPLICATIONS

The present application claims the benefit of Chinese Patent Application No. 201611008936.4 filed on Nov. 14, 2016, the contents of which are hereby incorporated by reference.

TECHNICAL FIELD

The present invention relates to the technical field of rock mechanics testing equipment, and particularly to a rock hollow cylinder torsional shear apparatus.

BACKGROUND ART

In the field of foundation engineering construction and resource/energy exploitation, such as transportation, water conservancy and hydropower and mining, it is required to construct a large number of deep-buried long and large tunnels (tunnels, laneways). TBM (full-section rock tunnel boring machine), by virtue of its unique advantages of safety, high efficiency, economy etc., becomes the optimal choice and the inevitable development orientation for construction of deep-buried long and large tunnels (tunnels, laneways). The excavation course of a TBM will cause continuous adjustment of the stress of the surrounding rock, prominently characterized by dramatic change in the main stress value together with wide-angle rotation of a principal stress axis. Under a condition of a deep-buried high stress, the aforesaid changes in the stress of the surrounding rock often result in the frequent occurrence of major engineering disasters such as high-strength rock burst, large deformation, machine jamming and the like, which are serious threats to the personnel and construction safety and cause huge economic losses. Therefore, in-depth reveal of surrounding rock breaking mechanism and mechanical characteristics under the combined condition of the change in the main stress value and the rotation of the principal stress axis of the surrounding rock when a TBM is tunneling in a deep stratum is the basic premise and scientific basis for the accurate prediction and reliable prevention and control of the aforesaid major engineering disasters, and is also a key factor to which major consideration should be given in the model selection of deep stratum TBMs and system adaptability design.

Among the existing domestic and foreign rock mechanics testing apparatuses, those capable of simulating a complex stress path include rock hollow cylinder torsional shear apparatuses. However, when they are working, the process of axial force application and the process of torque application will interfere with each other, resulting in reduction of the precision and reliability of the force exerted on a hollow rock sample; in addition, when a testing machine is in standby, there are safety problems such as rocking or collision of the force application assemblies suspended in the air.

DISCLOSURE OF THE INVENTION

The present invention provides a rock hollow cylinder torsional shear apparatus, to solve the technical problems of reduced test reliability and precision caused by mutual influence between the process of axial force application and the process of torque force application in the prior art.

In order to solve the above described technical problems, the present invention provides a rock hollow cylinder torsional shear apparatus which includes a frame, a lifting device, a bottom seat, a confining pressure barrel, an upper seat, a force transmission shaft, a force transmission shaft holder, a torque application structure and a controller.

The lifting device is fixed on the frame, and the bottom seat is fixed on the lifting device.

The confining pressure barrel is fixed on the bottom seat, and a lower pressure head, to which a bottom end of a sample is fixed, is provided in an inner cavity of the confining pressure barrel on the bottom seat.

The upper seat is fixed on an upper portion of the confining pressure barrel, and defines, together with the confining pressure barrel and the bottom seat, a sample reaction space.

The force transmission shaft has a middle portion embedded in the upper seat and a bottom portion located in the reaction space, and an upper pressure head, to which a top end of the sample is fixed, is provided at a bottom end of the force transmission shaft.

A piston is provided on a rod body of the middle portion of the force transmission shaft located in the upper seat, a force application oil cavity matched with the piston is provided in the upper seat, and the piston partitions the force application oil cavity into an upper force application oil cavity and a lower force application oil cavity.

An upper portion of the force transmission shaft is fixed on the frame by means of the force transmission shaft holder, to remain stationary relative to the frame in axial and radial directions.

The torque application structure is fixed on the frame and connected with the upper portion of the force transmission shaft to apply a torque.

The confining pressure barrel, the upper force application oil cavity and the lower force application oil cavity are all provided with oil conveying channels configured for being connected with an external hydraulic element.

The controller is connected with the torque application structure, the lifting device and the hydraulic element respectively.

The controller realizes chain control over the lifting device and the hydraulic element, so that when the hydraulic element supplies or discharges oil to or from the force application oil cavity to drive the reaction space to move up and down relative to the force transmission shaft, the lifting device moves along with the reaction space.

Further, the lifting device includes a hydraulic power element, a guide rail and a lifting support.

The guide rail is fixed on the frame, and the lifting support is fixed on the guide rail by means of a sliding block matched with the guide rail.

The hydraulic power element is fixed between the frame and the lifting support to drive the lifting support to move along the guide rail.

Further, the hydraulic power element includes a hydraulic jack.

Further, the oil conveying channels provided in the confining pressure barrel include:

oil conveying channels located on the upper seat and the bottom seat and communicating with the inner cavity of the confining pressure barrel; and an oil conveying channel located on the bottom seat and communicating with an inner cavity of a rock hollow cylinder sample.

Further, the upper pressure head and the lower pressure head are each provided thereon with an adhesion structure configured for adhering end portions of the sample to the upper pressure head and the lower pressure head, respectively.

Further, the force transmission shaft holder includes a first holder and a first flange screw thread.

The first holder has one end fixed on the frame, and the other end connected with the force transmission shaft by means of the first flange screw thread.

Further, the force transmission shaft holder further includes a second holder and a second flange screw thread.

The second holder has one end fixed on the frame, and the other end connected with the force transmission shaft by means of the second flange screw thread.

The first flange screw thread and the second flange screw thread are located at the middle portion and the upper portion of the force transmission shaft, respectively.

Further, the torque application structure includes a torque force transmission rod, a torque application oil cylinder and an oil cylinder fixing base.

The torque force transmission rod has one end connected with the upper portion of the force transmission shaft, and the other end connected with a piston head of the torque application oil cylinder by means of a joint bearing.

Further, the torque force transmission rod is fixed between the first flange screw thread and the second flange screw thread.

Further, sealing rings are provided between the bottom seat and the confining pressure barrel, between the upper seat and the confining pressure barrel, and between the upper seat and the force transmission shaft.

The one or more technical solutions provided in the embodiments of the present application at least have the following technical effects or advantages:

the rock hollow cylinder torsional shear apparatus provided by the embodiments of the present application innovates the torque and axial force applying modes of the torsional shear apparatuses, and coordinates the two operation processes to avoid mutual interference therebetween. Specifically, a force transmission shaft is fixed on a frame so as to remain stationary relative to the frame in axial and radial directions. A torque application structure is fixed on the frame and used as the force application fulcrum. A lifting device is provided to perform operation of lifting the main reaction space, so that the movable element in the axial force applying process shifts from the conventional force transmission shaft to the main reaction space. Thus, axial force application may be completed in the case that the force transmission shaft is neither axially or radially displaced. Meanwhile, in the torque force application operation, as the force transmission shaft is stationary relative to the frame both axially and radially and the torque force application assembly only applies a tangential torque to the force transmission shaft and is relatively stationary in axial and radial directions, the torque application operation and the axial force application operation is relatively independent from each other and thereby do not interfere with each other, which ensures reliability and precision of tests, avoids rigid connection between the torque application structure and the force transmission shaft in the existing structures, and avoids problems of force application precision, angle and stability being affected by the structural stress caused by the movement trend.

DETAILED DESCRIPTION OF EMBODIMENTS

By providing a rock hollow cylinder torsional shear apparatus, the embodiments of the present application solve the technical problem of reduced test reliability and precision caused by the mutual influence between the process of axial force application and the process of torque force application in the prior art, and achieve the technical effect of avoiding the mutual influence between the axial force application and torque force application.

In order to solve the above technical problem, the general idea of the technical solutions provided in the embodiments of the present application goes as follows:

By adjusting the mode of axial force application and keeping the force transmission shaft stationary relative to the frame, simultaneously making the frame used as the force application fulcrum of the torque application structure, and cooperating with a lifting device, the main reaction space structure can be lifted, so that the force transmission shaft undergoes relative movement in only one direction with respect to the torque application operation, thus, in an easy way, the two processes are independent from each other and do not interfere with each other.

To better understand the above technical solution, the technical solution will be described in detail below in conjunction with the drawings and specific embodiments. It should be understood that the embodiments of the present invention and the specific features in the embodiments are detailed description of the technical solution of the present application, rather than limiting the technical solution of the present application, and the embodiments of the present application and the features of the embodiments can be combined with each other if there is no conflict.

Figure 1:
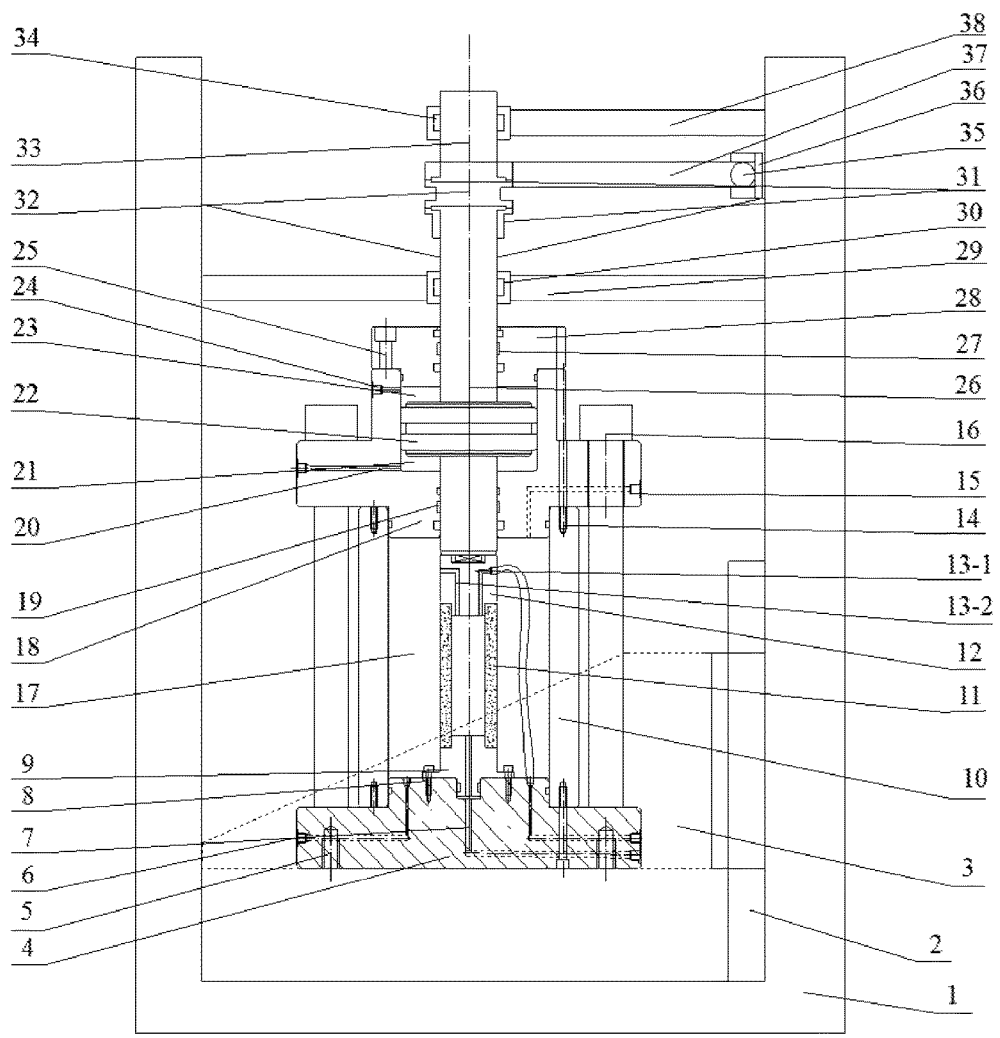
FIG. 1 is a structural schematic diagram of a rock hollow cylinder torsional shear apparatus provided by the present invention.
Figure 2:
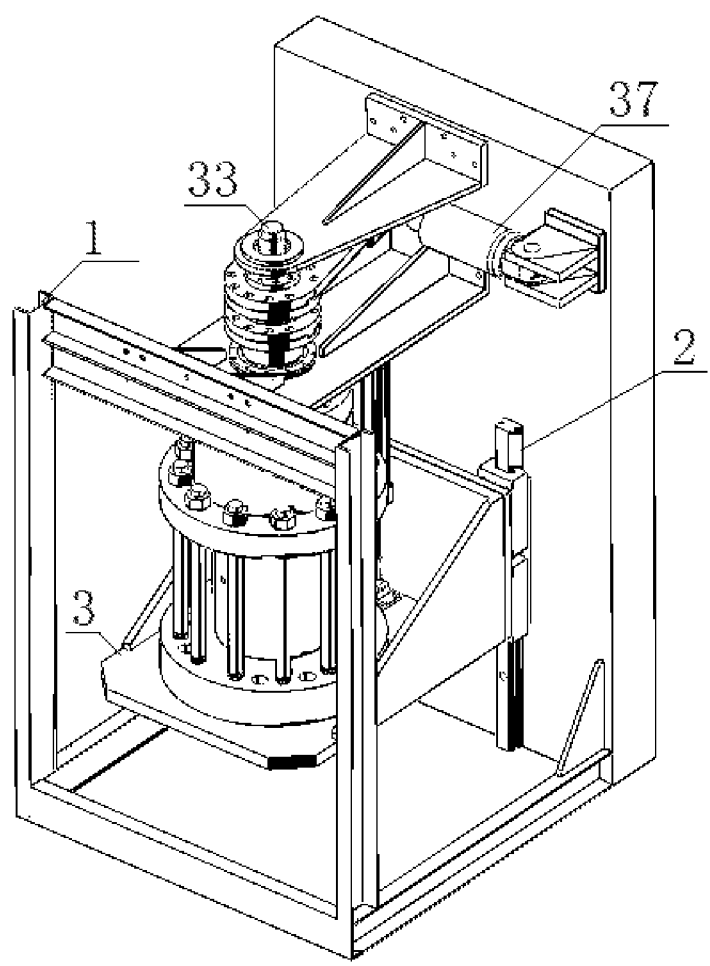
FIG. 2 is an outline drawing of the rock hollow cylinder torsional shear apparatus provided by the present invention.

Referring to FIG. 1 and FIG. 2, a rock hollow cylinder torsional shear apparatus includes a frame 1, a lifting device (2, 3), a bottom seat 4, a confining pressure barrel 10, an upper seat 18, a force transmission shaft 26, a force transmission shaft holder (29, 30, 34, 38), a torque application structure and a controller.

Specifically, the lifting device is fixed on the frame 1, and the bottom seat 4 is fixed on the lifting device by means of a bottom seat fixing bolt 5, so as to realize control of lifting and lowering of the bottom seat.

The confining pressure barrel 10 is fixed on the bottom seat 4, and a lower pressure head 9 for fixing the bottom end of a sample 11 is provided in the inner cavity 17 of the confining pressure barrel on the bottom seat 4 and is fixed on the bottom seat 4 by means of a lower pressure head fixing bolt 8.

The upper seat 18 is fixed on the upper portion of the confining pressure barrel 10 by means of an upper seat fixing bolt 14, and defines, together with the confining pressure barrel 10 and the bottom seat 4, a sample reaction space as a sample reaction environment space and a confining pressure application space. Moreover, the upper seat 18 and the bottom seat 4 are pressed tightly by means of a tensioning bolt 16.

Further, a force application oil cavity is usually defined by a groove on the upper seat 18 and a groove cover 28 and is fixed by means of a groove cover fixing bolt 25, which makes it easy for disassembly and maintenance.

The force transmission shaft 26 has a middle portion embedded in the upper seat 18, and a bottom portion located in the reaction space, and the bottom end of the force transmission shaft 26 is provided with an upper pressure head 12 for fixing the top end of the sample.

Two holes are provided in the upper pressure head 12, wherein one of the holes is a gas discharge hole 13-1 for an internal confining pressure-applying oil conveying channel 7; and the other one is a wire outlet hole 13-2 for a testing sensor, through which various types of testing sensors may be connected, as seen in FIG. 1.

A piston 22 is provided on a rod body of the middle portion of the force transmission shaft 26 located in the upper seat 18, a force application oil cavity matched with the piston is provided in the upper seat, and the piston 22 partitions the force application oil cavity into an upper force application oil cavity 23 and a lower force application oil cavity 21. In this way, the relative movement between the piston and the force application oil cavity is realized through the input and output of hydraulic oil, thus realizing force application and unloading operations.

The upper portion 33 of the force transmission shaft is fixed on the frame 1 by means of the force transmission shaft holder, to remain stationary relative to the frame in axial and radial directions. The torque application structure is fixed on the frame and connected with the upper portion of the force transmission shaft for applying a torque, so the force transmission shaft 26 is displaced with respect to the torque application structure along a tangential direction, with relative displacement in a structural model, such that axial force application and tangential force application are independent from each other, which avoids mutual influence.

The confining pressure barrel 10, the upper force application oil cavity 23 and the lower force application oil cavity 21 are all provided with oil conveying channels (24, 20, 15, 6, 7) for being connected with an external hydraulic element, for operations of applying confining pressure and hydraulic force.

The controller is connected with the torque application structure, the lifting device and the hydraulic element; the controller realizes chain control over the lifting device and the hydraulic element, so that when the hydraulic element supplies or drains oil to or from the force application oil cavity to drive the reaction space to move up and down relative to the force transmission shaft, the lifting device moves along with the reaction space.

Further, the lifting device includes a hydraulic power element, a guide rail 2 and a lifting support 3.

The guide rail 2 is fixed on the frame 1, and the lifting support 3 is fixed on the guide rail 2 by means of a sliding block matched with the guide rail 2.

The hydraulic power element is fixed between the frame 1 and the lifting support 3 to drive the lifting support to move along the guide rail.

Specifically, the hydraulic power element includes a hydraulic jack.

Further, the oil conveying channels arranged in the confining pressure barrel 10 include:

oil conveying channels (6, 15) located on the upper seat 18 and the bottom seat 4 and communicating with the inner cavity of the confining pressure barrel; and an oil conveying channel 7 located on the bottom seat 4 and communicating with the inner cavity of the a rock hollow cylinder sample 11.

Further, the upper pressure head 12 and the lower pressure head 9 are each provided thereon with an adhesion structure for adhering end portions of the sample to the upper pressure head and the lower pressure head, respectively.

Further, the force transmission shaft holder includes a first holder 38 and a first flange screw thread 34.

The first holder 38 has one end fixed on the frame 1, and the other end connected with the force transmission shaft by means of the first flange screw thread 34.

Further, the force transmission shaft holder further includes a second holder 29 and a second flange screw thread 30.

The second holder 29 has one end fixed on the frame 1, and the other end connected with the force transmission shaft 26 by means of the second flange screw thread 30.

The first flange screw thread 30 and the second flange screw thread 34 are located at the middle portion and the upper portion of the force transmission shaft, respectively, thereby forming two fulcra and ensuring the stability of the force transmission shaft.

Further, the torque application structure includes a torque force transmission rod, a torque application oil cylinder 37 and an oil cylinder fixing base 36.

The torque force transmission rod has one end connected with the upper portion 33 of the force transmission shaft, and the other end connected with the piston head of the torque application oil cylinder 37 by means of a joint bearing.

Preferably, the tail of the torque application oil cylinder 37 is pivotally connected with the oil cylinder fixing base 36 through a pivot shaft 35.

Further, the torque force transmission rod is fixed between the first flange screw thread 34 and the second flange screw thread 30, so as to ensure torque application without affecting the posture of the force transmission shaft.

Further, sealing rings 27, 19 are provided between the bottom seat and the confining pressure barrel, between the upper seat and the confining pressure barrel, and between the upper seat and the force transmission shaft.

Preferably, the force transmission shaft 26 may further be connected with another force transmission shaft through a shaft coupling 31. A torque sensor 32 is provided on the shaft coupling, and the another force transmission shaft is connected with the torque application structure, so as to monitor in real time the torque at the terminal, feed back the force application of the torque application oil cylinder 37, and ensure the precision of the force application.

The working process of the torsional shear apparatus is specifically described below.

Specifically, an indoor test is carried out for the present invention according to the following steps:

Step 1: mounting a hollow rock sample 11 by: lowering the lifting support 3 to the lowest point; placing a measuring instrument inside the hollow rock sample 11 before mounting the sample; gluing, with super glue, one end of the hollow rock sample 11 to the lower pressure head 9 and the other end to the upper pressure head 12; fixing the hollow rock sample 11, coated with an anti-permeation leather tube, on the bottom seat 4 with a lower pressure head fixing bolt 8; and placing relevant measuring devices inside and outside the hollow rock sample 11;

Step 2: controlling, by the controller, the bottom seat 4 to rise such that the confining pressure barrel 10 contacts with the upper seat 18, at which moment, the groove on the upper pressure head 12 is engaged with the raised head at the lower portion of the force transmission shaft 26, thus completing the mounting of the hollow rock sample;

Step 3: implementing loading by: controlling, by the controller, a first external confining pressure-applying oil conveying channel 6 and a second external confining pressure-applying oil conveying channel 15 to convey oil to the inner cavity 17 of the confining pressure barrel, to apply an external confining pressure, and an internal confining pressure-applying oil conveying channel 7 to convey oil to the cavity inside the hollow rock sample 11 to provide an internal confining pressure; axially loading the oil conveying channel 24 to convey oil to the upper force application oil cavity 23, to push the groove cover 28 to make the entire testing machine move upwards (the upper portion 33 of the force transmission shaft stays stationary) to apply an axial force; and making the groove on the upper pressure head 12 engaged with the raised head at the lower portion of the force transmission shaft 26, and pushing the force transmission shaft 26 by the torque application oil cylinder 37 to do circular motion, thus providing a torque to the hollow rock sample; and Step 4: unloading and dismounting the sample, wherein the method of unloading the internal and external confining pressures is substantially the same as the methods of loading the internal and external confining pressures, viz. performing unloading by controlling oil pumping through the controller, wherein oil is conveyed to the lower force application oil cavity 21 by axially unloading the oil conveying channel 20, to push the upper seat 18 to make the entire testing machine to move downwards, so as to unload the axial pressure; the torque can be unloaded just by reverse movement of the torque application oil cylinder 37; and after unloading, the controller is used to control the lifting support 3 to descend, and then the hollow rock sample is dismounted.

The one or more technical solutions provided in the embodiments of the present application at least have the following technical effects or advantages:

the rock hollow cylinder torsional shear apparatus provided by the embodiments of the present application innovates the torque and axial force applying modes of the torsional shear apparatuses, and coordinates the two operation processes to avoid mutual interference therebetween. Specifically, the force transmission shaft is fixed on the frame so as to remain stationary relative to the frame in axial and radial directions. The torque application structure is fixed on the frame and used as the force application fulcrum. The lifting device is provided to perform operation of lifting the main reaction space so that the movable element in the axial force applying process shifts from the conventional force transmission shaft to the main reaction space. Thus, axial force application may be completed in the case that the force transmission shaft is neither axially or radially displaced. Meanwhile, in the torque force application operation, as the force transmission shaft is stationary relative to the frame in axial and radial directions and the torque force application assembly only applies a tangential torque to the force transmission shaft and is thus relatively stationary in axial and radial directions, the torque application operation and the axial force application operation is relatively independent from each other and thereby do not interfere with each other, which ensures reliability and precision of tests, avoids rigid connection between the torque application structure and the force transmission shaft in the existing structures, and avoids problems of the force application precision, angle and stability being affected by the structural stress caused by the movement trend.

Finally, it should be noted that the above embodiments are only used to illustrate the technical solutions of the present invention, rather than limit the same. While the present invention has been described in detail with reference to the embodiments, it should be understood, by those of ordinary skill in the art, that modifications or equivalent replacements can be made to the technical solutions of the present invention without departing from the spirit and scope of the technical solutions of the present invention, which shall all be covered by the scope of the claims of the present invention.

The invention claimed is:

1. A rock hollow cylinder torsional shear apparatus, comprising a frame, a lifting device, a bottom seat, a confining pressure barrel, an upper seat, a force transmission shaft, a force transmission shaft holder, a torque application structure and a controller,
   wherein the lifting device is fixed on the frame, and the bottom seat is fixed on the lifting device;
   the confining pressure barrel is fixed on the bottom seat, and a lower pressure head, to which a bottom end of a sample is fixed, is provided in an inner cavity of the confining pressure barrel on the bottom seat;
   the upper seat is fixed on an upper portion of the confining pressure barrel, and configured to define, together with the confining pressure barrel and the bottom seat, a sample reaction space;
   the force transmission shaft has a middle portion embedded in the upper seat, and a bottom portion located in the reaction space, and a bottom end of the force transmission shaft is provided with an upper pressure head to which a top end of the sample is fixed;
   a piston is provided on a rod body of the middle portion of the force transmission shaft located in the upper seat, a force application oil cavity matched with the piston is provided in the upper seat, and the piston is configured to partition the force application oil cavity into an upper force application oil cavity and a lower force application oil cavity;
   an upper portion of the force transmission shaft is fixed on the frame by means of the force transmission shaft holder, to retain stationary relative to the frame in axial and radial directions;
   the torque application structure is fixed on the frame, and connected with the upper portion of the force transmission shaft to apply a torque;
   the confining pressure barrel, the upper force application oil cavity and the lower force application oil cavity are all provided with oil conveying channels configured for being connected with an external hydraulic element; and
   the controller is connected with the torque application structure, the lifting device and the hydraulic element respectively;
   wherein the controller is configured to realize chain control over the lifting device and the hydraulic element, so that when the hydraulic element supplies or discharges oil to or from the force application oil cavity to drive the reaction space to move up and down relative to the force transmission shaft, the lifting device moves along with the reaction space.

2. The rock hollow cylinder torsional shear apparatus according to claim 1, wherein the lifting device comprises a hydraulic power element, a guide rail and a lifting support, wherein the guide rail is fixed on the frame, and the lifting support is fixed on the guide rail by means of a sliding block matched with the guide rail; and
   the hydraulic power element is fixed between the frame and the lifting support to drive the lifting support to move along the guide rail.

3. The rock hollow cylinder torsional shear apparatus according to claim 2, wherein the hydraulic power element comprises a hydraulic jack.

4. The rock hollow cylinder torsional shear apparatus according to claim 3, wherein the oil conveying channels provided in the confining pressure barrel comprise:
   oil conveying channels located on the upper seat and the bottom seat, and communicating with the inner cavity of the confining pressure barrel; and
   an oil conveying channel located on the bottom seat and communicating with an inner cavity of a rock hollow cylinder sample.

5. The rock hollow cylinder torsional shear apparatus according to claim 4, wherein the upper pressure head and the lower pressure head are each provided thereon with an adhesion structure configured for adhering end portions of the sample to the upper pressure head and the lower pressure head, respectively.

6. The rock hollow cylinder torsional shear apparatus according to claim 5, wherein sealing rings are provided between the bottom seat and the confining pressure barrel, between the upper seat and the confining pressure barrel, and between the upper seat and the force transmission shaft.

7. The rock hollow cylinder torsional shear apparatus according to claim 4, wherein the force transmission shaft holder comprises a first holder and a first flange screw thread,
   the first holder has one end fixed on the frame, and the other end connected with the force transmission shaft by means of the first flange screw thread.

8. The rock hollow cylinder torsional shear apparatus according to claim 7, wherein the force transmission shaft holder further comprises a second holder and a second flange screw thread,
   the second holder has one end fixed on the frame, and the other end connected with the force transmission shaft by means of the second flange screw thread;
   wherein the first flange screw thread and the second flange screw thread are located at the middle portion and the upper portion of the force transmission shaft, respectively.

9. The rock hollow cylinder torsional shear apparatus according to claim 8, wherein the torque application structure comprises a torque force transmission rod, a torque application oil cylinder and an oil cylinder fixing base,
   wherein the torque force transmission rod has one end connected with the upper portion of the force transmission shaft, and the other end connected with a piston head of the torque application oil cylinder by means of a joint bearing.

10. The rock hollow cylinder torsional shear apparatus according to claim 9, wherein the torque force transmission rod is fixed between the first flange screw thread and the second flange screw thread.

11. The rock hollow cylinder torsional shear apparatus according to claim 10, wherein sealing rings are provided between the bottom seat and the confining pressure barrel, between the upper seat and the confining pressure barrel, and between the upper seat and the force transmission shaft.

12. The rock hollow cylinder torsional shear apparatus according to claim 9, wherein sealing rings are provided between the bottom seat and the confining pressure barrel, between the upper seat and the confining pressure barrel, and between the upper seat and the force transmission shaft.

13. The rock hollow cylinder torsional shear apparatus according to claim 8, wherein sealing rings are provided between the bottom seat and the confining pressure barrel, between the upper seat and the confining pressure barrel, and between the upper seat and the force transmission shaft.

14. The rock hollow cylinder torsional shear apparatus according to claim 7, wherein sealing rings are provided between the bottom seat and the confining pressure barrel, between the upper seat and the confining pressure barrel, and between the upper seat and the force transmission shaft.

15. The rock hollow cylinder torsional shear apparatus according to claim 4, wherein sealing rings are provided between the bottom seat and the confining pressure barrel, between the upper seat and the confining pressure barrel, and between the upper seat and the force transmission shaft.

16. The rock hollow cylinder torsional shear apparatus according to claim 3, wherein sealing rings are provided between the bottom seat and the confining pressure barrel, between the upper seat and the confining pressure barrel, and between the upper seat and the force transmission shaft.

17. The rock hollow cylinder torsional shear apparatus according to claim 2, wherein sealing rings are provided between the bottom seat and the confining pressure barrel, between the upper seat and the confining pressure barrel, and between the upper seat and the force transmission shaft.

18. The rock hollow cylinder torsional shear apparatus according to claim 1, wherein sealing rings are provided between the bottom seat and the confining pressure barrel, between the upper seat and the confining pressure barrel, and between the upper seat and the force transmission shaft.

* * * * *